United States Patent [19]

Blytas et al.

[11] 4,024,400

[45] May 17, 1977

[54] MONITORING METALS CONCENTRATION IN FLUID STREAMS

[75] Inventors: George C. Blytas; Richard M. Curtis, both of Houston, Tex.

[73] Assignee: Shell Oil Company, Houston, Tex.

[22] Filed: May 13, 1976

[21] Appl. No.: 685,952

[52] U.S. Cl. .............................. 250/432 R; 250/460
[51] Int. Cl.$^2$ ....................................... G01N 21/24
[58] Field of Search .......... 250/383, 272, 273, 303, 250/308, 432 R, 460

[56] References Cited

UNITED STATES PATENTS

| | | | |
|---|---|---|---|
| 3,004,163 | 10/1961 | Edholm | 250/272 |
| 3,254,214 | 5/1966 | Bennett | 250/383 |
| 3,449,567 | 6/1969 | Olivier et al. | 250/383 |

*Primary Examiner*—Harold A. Dixon
*Attorney, Agent, or Firm*—Ronald R. Reper

[57] ABSTRACT

A method and apparatus is provided for monitoring metals concentration in fluid streams, and particularly for detecting rapid changes in metal concentrations in hydrocarbon streams.

10 Claims, 1 Drawing Figure

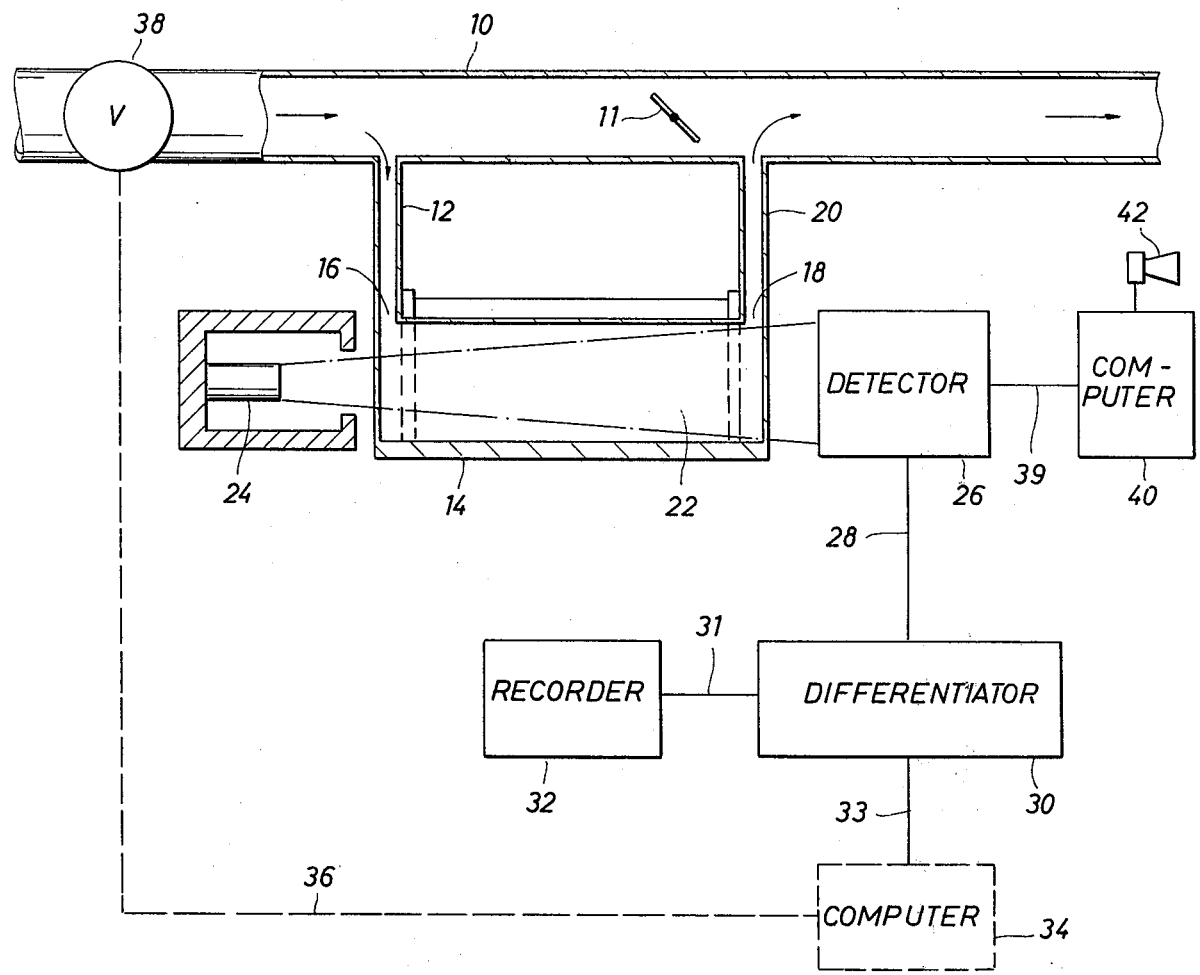

MONITORING METALS CONCENTRATION IN FLUID STREAMS

BACKGROUND OF THE INVENTION

The presence of metals in fluid streams is deleterious for many uses. For example, governmental regulations now require the marketing of gasolines having at most 0.05 grams of lead per gallon in order to prevent poisoning of noble metal containing catalytic mufflers installed on internal combustion engines. Although non-leaded gasolines may be produced at petroleum refineries with adequately low lead level to meet the legal requirement, occasionally the gasolines will absorb small but significant amounts of lead compounds from storage; or by inadvertent contamination during transportation in lead contaminated tanks or pipelines to exceed this limit.

In a like manner, metals such as lead and copper may be found in hydrocarbon distillate fuels owing to contamination during shipping or storage. Those metals in concentrations above a few parts per million tend to promote deposit of solids, cause corrosion and otherwise accelerate maintenance problems of the engines, turbines and the like in which the fuel is combusted. Also, in the refining of petroleum, metals such as lead, nickel and vanadium are deleterious to many catalytic processes particularly those in which hydrogen is consumed or generated. Often in such processes the liquid or vaporized feed is first passed through a "guard bed" of metals adsorbent, in order to protect the catalyst. However, with heavy contamination the guard bed may unexpectedly become exhausted. Accordingly, it would be highly desirable to be able to continuously monitor fluid streams to detect metals contamination at an early time, in order to be able to control the fluid flow and prevent or at least minimize deleterious consequences thereof.

SUMMARY OF THE INVENTION

The invention provides a method for monitoring metal concentration of a fluid stream containing metal, which comprises passing at least a portion of said stream through a metal sorbent to sorb said metal from said stream, said sorbent having an X-ray mass absorbtion coefficient lower than that of the metals to be monitored, passing an X-ray beam through said sorbent, measuring the intensity of the X-ray beam which has passed through the sorbent to produce a detector signal in response to the intensity of said measured X-ray beam;

differentiating logarithmically the detector signal occurring in a predetermined time period to obtain a derivative signal related to the metal concentration in said fluid stream, and supplying said derivative signal to information means to obtain information related to the metal concentration in said fluid stream.

The invention also provides a method for controlling the flow rate of the fluid stream in response to the derivative signal obtained as above.

The invention further provides a metals-level monitoring system for determining change in the level of metal concentrations in fluid streams which comprises in combination:

sample holder adapted to contain a metal sorbent, said holder having an inlet opening and an outlet opening for establishing a flow of fluid therethrough;

X-ray source means operatively engaging said sample holder for emitting an X-ray beam through said metal sorbent in said sample holder;

X-ray beam detection means disposed in relation to said sample holder to receive X-rays from said X-ray source means which have passed through the sorbent in said sample holder, and to generate a signal in response to the intensity of said received X-rays;

signal differentiation means coupled to said X-ray beam detection means to receive the signal therefrom and to logarithimically differentiate the signal in a predetermined time period, to produce a detection signal related to the change in intensity of the received X-rays; and signal information means coupled to said signal differentiating means to inform about changes in the intensity of X-rays detected in a predetermined time period.

BRIEF DESCRIPTION OF THE DRAWING

The present invention will be more easily understood from the following detailed description taken in conjunction with the attached drawing which is a blocked diagram of the system according to the invention and is used for practicing the method of the invention.

DESCRIPTION OF THE PREFERRED EMBODIMENTS

Referring now to the drawing, there is shown a block diagram of the system of the invention suitable for practicing the method of the invention. There is shown a fluid stream which can be e.g. a gasoline stream going to storage, a distillate gas oil feed to a stationary turbine power plant, a vaporized mixture of hydrocarbons and hydrogen going to a catalytic reactor, a heavy residual oil exiting a demetallization guard bed, or a metals-containing aqueous stream.

At least a portion of the fluid stream 10 is passed via line 12 to sample holder 14 having an inlet 16. The fluid exits sample holder 14 via exit 18 and line 20 and may be returned to line 10 or disposed of otherwise as desired via means not shown. Flow rate may be adjusted via valve means 11 in line 10 or by a pump (not shown) on 12 or on line 20. Sample holder 14 contains metals selective sorbent 22 having an X-ray absorption coefficient lower than that of the metal to be detected. Suitable sorbents include, for example, ion exchange resins, molecular sieves, activated carbon which may be impregnated with reagents such as tin chloride or otherwise chemically treated to increase selectivity for the selected metal or metals to be monitored, and the like. A particularly preferred sorbent is acidified active carbon prepared according to U.S. Pat. application Ser. No. 673,311, filed Apr. 5, 1976. Preferably, the sorbent and/or shape of the sample holder will be selected to have an X-ray mass sorbtion coefficient of less than one-half and more preferably about one-third or less than that of the metals to be monitored. X-ray source means 24 is mounted to operationally engage sample holder 14 to emit an X-ray beam through the metal sorbent 22 to X-ray detection means 26 mounted to detect X-rays passing through sorbent 22. Preferably X-ray source 24 and sample holder 14 are shielded e.g., with lead sheet to avoid or substantially reduce any health hazard arising from the X-ray irradiation. The sample holder which may be constructed of any material impervious to the contained fluid may, if desired, be constructed with "windows" of materials more transparent to X-rays such as aluminum, beryllium reinforced plastic and the like to facilitate sensitivity of the detector system. Choice of the particular X-ray energy source will, in part, be determined by the particular metal and sorbent employed. For example, when monitoring for lead a suitable sorbent might be the hydrogen form of ultra stabilized Y Faujasite available from Davison in which case X-ray energies of 16.5 KeV up to about 25 KeV may be used. An advantage of using X-ray energies in the range near 25 KeV is that the mass absorbtion coefficients of carbon and hydrogen are nearly equal; thus where the fluid to be monitored is a hydrocarbon, the efficiency of the system is independent of the carbon/hydrogen ratio in the fluid. Exemplary sources of such X-ray energies are cadmium 109, Iodine 125, Tin 199m and Tellurium 125m. Any type of detector or detection system that supplies an electrical signal related to instantaneous changes in X-ray intensity can be used. This may be an ion chamber or scintillator in combination with e.g. a photomultiplier, amplifier and scaler. The electrical signal from the detection system is supplied via a coupling 28 such as a coaxial cable, to differentiator 30. Differentiator 30 may be e.g. a dual scaler coupled to simple minicomputer. The signal differentiator converts the detector signal into its first logarhithmic derivative with respect to the time of measurement, which time may be in minutes, seconds or to provide essentially continuous monitoring, in fractions of a second. The differentiator 30 is connected by lead 31 to signal information means 32 such as a strip chart recorder or warning signal. The system is envisioned as operating at some nominal metals level and energizing a warning signal such as a light, bell, horn or the like, whenever the rate of change of metals level in the fluid stream exceeds a predetermined value.

In a preferred embodiment the detector is connected by lead 39 to computer 40 which compares the detector signal with a signal determined by the level of signal first received through the fresh sorbent, and when, as the system is used, the on-going signal falls to 20% and preferably 25% of the original signal, computer 40 via lead 41 triggers alarm 42, or activates sequencing of new sorbent in the cell holder (not shown) as will be subsequently described.

To facilitate better understanding of the system theory of operation for the system will be briefly described.

THEORY OF OPERATION

The transmission of collimated X-rays through a cell of thickness, L, of average density, $b$, and mass absorption coefficient, $\mu$, is given by the relations:

$$I = I_o e^{-\mu bL} \tag{1}$$

where $I_o$ and $I$ are the intensities of entering and exiting beams, (counts or photons per unit time). In equation (1), $\mu = \Sigma \mu_i W_i$ is the sum of weight fraction weighted $\mu$'s of the elements in the energy sorbing medium.

As the cell adsorbs a heavy metal, both $\mu$ and $b$ will change. But the change in $b$ will be small (typically 2%) and can thus be neglected. Then if $\mu_A$ refers to the fresh system and $\mu_B$ to the heavy metal component, $\mu = \mu_A(1 - X) + \mu_B(X)$ where X is the weight fraction of metal. Hence $$I = I_o e^{-[\mu_A + X(\mu_B - \mu_A)]bL} \text{ and since } \mu_B > \mu_A \tag{2}$$

$$I \approx I_o e^{-[\mu_A + \mu_B X]bL} = I_1 e^{-\mu_B bLX}$$

where $I_1 = I_o e^{-\mu_A bL}$ corresponds to the intensity with a fresh cell.

The logarithmic derivative of equation (2) is directly proportional to the metal input per unit time and is independent of the pre-existing metal content in the absorber bed. Thus, it is convenient to measure $d \ln I$ rather than I itself.

$$d \ln I = -bL \, \mu_B \, dX \tag{3}$$

For a finite time interval, T, the measured quantity, i.e., the signal S is:

$$S = \frac{\Delta I}{I} = -bL \, \mu_B \, \Delta_X \tag{4}$$

As noted above, the system will typically operate at some nominal level of X and may provide a warning signal whenever $\Delta X$ exceeds a preset value.

The above system can be fabricated from commercially available parts or a specially designed system can be used.

The signal from the differentiator 30 can be supplied via lead 33 to a simple computer 34, shown in the drawing in phantom, which in turn controls the flow of the fluid stream. For example, the computer may consist of a conventional process controller 34 whose set point is adjusted for a predetermined metal level in the stream and whose output controls the flow rate of fluid stream 10 via lead 36 and control valve 38.

The system is suitable for use with aqueous or non-aqueous or gaseous systems, however, will function best if the fluid mentioned is in a homogeneous physical state. This may be achieved by using conventional means such as heating e.g. to dissolve undissolved water in a hydrocarbon stream, or to evaporate partially condensed fluids in a vaporous feed stream, or, in the alternative cooling the feed stream to condense a partially vaporized feed to a homogeneous phase liquid.

As will be obvious, the effective life of the metal sorbent will depend upon a number of factors including the particular sorbent, the size of the sorbent holder, the quantity of metals in the feed and the like. For some applications, it will be desirable to have a plurality of holders available for manual or automatic replacement of cell holder 14. The replacement holder may e.g. be located on a bar or tray to slidably replace a holder containing exhausted sorbent or alternatively be disposed on a rotable carrousel to rotatably replace said exhausted sorbent containing holder. It is also possible to arrange two or more holders and detectors to receive X-rays from a common source and to cause the fluid to be monitored to flow solely through a first holder, and wherein only the output of the detector for said first holder is operatively engaging the differentiator, and upon exhaustion of said first holder to cause the flow of fluid to flow solely to a second holder and to simultaneously switch the differentiator solely the detector associated with the second holder.

To provide information when the sorbent is exhausted the system preferably includes a comparator circuit operatively engaging the detector to trigger an alarm such as a light, buzzer and the like when the intensity of the X-rays received on the detector falls off to a small percentage. e.g. 20% and preferably 25% of the intensity originally received through the fresh sorbent.

The metals to be monitored will ordinarily be those having an atomic number above about 23, e.g. vanadium and chromium, iron, nickel, cobalt, copper, zinc, mercury, tin, lead and the like. The metals may be as such or in the form of organic or inorganic compounds, soluble or insoluble in the fluid. The nature of the metals to be measured will at least partly determine the sorbent to be used in the system. For example, for measuring dissolved lead, copper, and nickel compounds in hydrocarbons a preferred sorbent is activated carbon which has been acidified with i.e. strong acidizing medium as described in previously mentioned U.S. Pat. application Ser. No. 673,311.

Finely divided metals and undissolved compounds such as iron and rust might be sorbed into glass wool or filter media of suitable porosity. For soluble metal compounds in an aqueous fluid, an ion exchange resin could be a suitable sorbent.

The invention will be better understood by reference to the following example.

EXAMPLE

From a kerosene range hydrocarbon feed to a stationary turbine installation and typically containing 0.1 ppm each of dissolved lead and copper, a representative slip stream is passed through a system as shown in the drawing. The X-ray source emits an X-ray intensity of $3.5 \times 10^6$ photons/minute through 2 cm of activated carbon which is treated with a mixture of concentrated nitric and sulfuric acids for 20 minutes, washed free of the acids and is dried before being placed in the sorbent holder. The feed flow rate is 22 grams/cm²/minute through the sorbent. The detector signal is counted for 20 minutes to obtain an average count rate. The difference between consecutive average count rates may be divided by the average of the two consecutive average count rates, to provide the logarithmic derivative which represents the desired signal. Substantially equivalent mathematical treatment may also be employed to obtain the desired signal, e.g. subtracting from the number 1 the ratio of the second average count rate to the first average count rate, since the differences typically are very small. As the metals content of the stream does not vary appreciably, the recorded signal is a straight line on the strip chart recorder, and the expected sorbent life is one week. The system is programmed such that if the total metals content rises to 2 ppm a warning buzzer is tripped, and computer 36 sends a signal to close valve 38 whereby flow of the high metals containing kerosene is stopped. Typically where continuous operation of the turbine is necessary an alternate source of feed (not shown) is provided automatically upon cessation of the flow being monitored. In an alternative embodiment the computer signal does not operate a valve as shown in the drawing, but rather opens a source of metals-free kerosene to mix with and dilute the undesirably high metals-containing feed.

What is claimed is:

1. A method for monitoring metal concentration of a fluid stream containing metals, which comprises
    passing at least a portion of the said stream through a metals selective sorbent to sorb said metals, said sorbent having an X-ray mass absorbtion coefficient lower than that of the metals in said stream;
    passing an X-ray beam through said sorbent;
    detecting the intensity of the X-ray beam which has passed through said sorbent, to produce a detector signal in response to the intensity of said detected X-ray beam;
    differentiating logarithmically the detector signal occurring in a predetermined time period to obtain a derivative signal related to the metal concentration in the fluid stream; and
    supplying said derivative signal to information means to obtain information related to the metal concentration in said fluid stream.

2. A method as in claim 1 wherein the fluid is a liquid.

3. A method as in claim 2 wherein the liquid is a hydrocarbon.

4. A method as in claim 2 wherein the liquid is an aqueous stream.

5. A method for controlling the passage of a fluid stream through a conduit on the basis of suitable concentration of selected metal in said fluid stream, which method comprises
    passing a portion of the fluid stream in conduit through a sorbent to sorb the metal, said sorbent having an X-ray absorbtion coefficient lower than that of sorbed metals;
    passing an X-ray beam through said sorbent;
    detecting the intensity of the X-ray beam which has passed through said sorbent to produce a detector signal in response to the intensity of said X-ray beam;
    differentiating logarithmically the detector signal occurring in a predetermined time period to obtain a derivative signal related to the metal concentration in the hydrocarbon stream;
    comparing the differentiated signal with a preset signal representing the desired metal concentration in the hydrocarbon stream over a predetermined time period to obtain an error signal, and
    controlling the passage of said hydrocarbon stream through the conduit in response to said error signal.

6. A method as in claim 5 wherein the fluid is a liquid.

7. A method as in claim 6 wherein the liquid is a hydrocarbon.

8. A method as in claim 6 wherein the liquid is aqueous.

9. A metals level monitoring system for determining changes in the level of metals content in fluid streams which comprises in combination
    sample holder adapted to contain a metal sorbent, said holder having an inlet and an outlet for establishing a flow of fluid therethrough;
    X-ray source means operatively engaging said sample holder for emitting an X-ray beam through said metal sorbent in said sample holder;
    X-ray beam detection means disposed in relation to said sample holder to receive X-rays from said X-ray source means which have passed through the sorbent in said sample holder and to generate a signal in response to the intensity of said received X-rays;
    signal differentiation means coupled to the detector to receive the signal therefrom and to logarithmically differentiate the signal so occurring in a predetermined time period, to produce a detection signal related to the change in intensity of the received X-rays; and signal information means coupled to said signal differentiating means to inform about changes in X-ray detection occurring in a predetermined time period.

10. A system as in claim 9 wherein the X-ray source means provides X-ray energies in the range from about 16.5 KeV to about 25 KeV.

* * * * *